United States Patent
Sarvazyan et al.

[11] Patent Number: 6,142,959
[45] Date of Patent: Nov. 7, 2000

[54] DEVICE FOR PALPATION AND MECHANICAL IMAGING OF THE PROSTATE

[75] Inventors: Armen P. Sarvazyan, Lambertville; Vladimir Egorov, Plainsboro, both of N.J.

[73] Assignee: ArMed L.L.C., Minneapolis, Minn.

[21] Appl. No.: 09/359,200

[22] Filed: Jul. 22, 1999

Related U.S. Application Data

[63] Continuation-in-part of application No. 08/872,559, Jun. 10, 1997, Pat. No. 5,922,018, which is a continuation-in-part of application No. 08/607,645, Feb. 27, 1996, Pat. No. 5,785,663, which is a continuation-in-part of application No. 07/994,109, Dec. 21, 1992, Pat. No. 5,524,636.

[51] Int. Cl.[7] .................................................. A61B 5/103
[52] U.S. Cl. ............................................................ 600/587
[58] Field of Search .................................. 600/437, 438, 600/439, 440, 442, 443, 444, 445, 446, 561, 587

[56] References Cited

U.S. PATENT DOCUMENTS

| | | | |
|---|---|---|---|
| 4,250,894 | 2/1981 | Frei et al. | 128/774 |
| 4,711,248 | 12/1987 | Steuer et al. | 128/748 |
| 4,722,348 | 2/1988 | Ligtenberg et al. | 128/675 |
| 4,809,710 | 3/1989 | Williamson | 128/748 |
| 4,869,265 | 9/1989 | McEwen | 128/774 |
| 4,893,634 | 1/1990 | Kulik et al. | 128/748 |
| 4,947,851 | 8/1990 | Sarvazyan et al. | 128/660.02 |
| 5,067,491 | 11/1991 | Taylor, II et al. | 128/748 |
| 5,107,837 | 4/1992 | Ophir et al. | 128/660.01 |
| 5,170,790 | 12/1992 | Lacoste et al. | 128/660.01 |
| 5,178,148 | 1/1993 | Lacoste et al. | 128/660.03 |
| 5,265,612 | 11/1993 | Sarvazyan et al. | 128/660.01 |
| 5,293,870 | 3/1994 | Ophir et al. | 128/660.01 |
| 5,423,332 | 6/1995 | Zirps et al. | 128/774 |
| 5,474,070 | 12/1995 | Ophir et al. | 128/660.01 |
| 5,522,399 | 6/1996 | Wilk et al. | 128/748 |
| 5,526,829 | 6/1996 | Khoury | 128/748 |
| 5,836,894 | 11/1998 | Sarvazyna | 600/587 |
| 5,922,018 | 7/1999 | Sarvazyan | 600/587 |

OTHER PUBLICATIONS

D. J. Rubens, MD et al., "Sonoelasticity Imaging of Prostate Cancer: In Vitro Results", Journal of Radiology, 195, No. 2.

*Primary Examiner*—Cary O'Connor
*Assistant Examiner*—Charles Marmor, II
*Attorney, Agent, or Firm*—Mathews, Collins, Shepherd & Gould, P.A.

[57] ABSTRACT

The present invention relates to a method for mechanically imaging the prostate with a prostate examination device. In the method, position data and pressure response data are acquired along predetermined trajectories overlaying the prostate by periodic pressing or sliding of a pressure sensor assembly attached to a probe against the prostate. In a preferred embodiment, the prostate examination device comprises a probe sized to fit within the rectum and having a head connected by a shaft to a handle. A support is connected to the probe for providing a point of rest for the shaft during the prostate examination. As the pressure sensor assembly is pressed against and moved over the prostate, it generates signals in response to forces imposed on the pressure sensor assembly. A positioning system is coupled to the support and probe for determining position data of the pressure sensor assembly during prostate examination. An electronic unit receives the data from the pressure sensor assembly and the position data from the positioning system and determines a structure of the prostate.

32 Claims, 17 Drawing Sheets

DEVICE FOR PALPATION AND MECHANICAL IMAGING OF THE PROSTATE

CROSS REFERENCE TO RELATED APPLICATION

This application is a continuation-in-part of U.S. patent application Ser. No. 08/872,559 filed Jun. 10, 1997, and issued as U.S. Pat. No. 5,922,018 which is a continuation-in-part of U.S. patent application No. 08/607,645 filed Feb. 27, 1996 and issued as U.S. Pat. No. 5,785,663 which is a continuation-in-part of U.S. patent application No. 07/994,109 filed Dec. 21, 1992 and issued as U.S. Pat. No. 5,524,636 on Jun. 11, 1996. The full disclosures of the above-described applications and the issued patents are incorporated herein by reference.

BACKGROUND OF THE INVENTION

1. Field of the Invention

The present invention relates to a method and device for mechanically imaging the prostate.

2. Description of Related Art

Conventional methods for early detection of prostate cancer include digital rectal examination (DRE). Digital rectal examination or palpation, that is an examination using the sense of touch, is based on the significant differences in elasticity of normal tissues and certain lesions. Palpation has been a commonly used test by general practitioners and specialists and is recommended as a part of an annual general preventive physical examination for all men 40 years of age and older. The effectiveness and reliability of palpation is dependent on the level of skill of the examiner, since the finger as an instrument does not provide any quantitative information, and therefore the examiner must instinctively relate what he/she senses by the finger to their previous experience with palpation, as described in Littrup et al., *The Benefit and Cost of Prostate Cancer Early Detection*, CA Cancer Journ. for Clinicians, Vol. 43, pp. 134–149 (1993). It has been found that the disagreement between the palpatory findings of experienced urologists is about 20%, as described in Smith et al., *Interexaminer Variability of Digital Rectal Examination in Detecting Prostate Cancer*, Urology, Vol. 45, pp. 70–74 (1995). The disagreement within inexperienced examiners (who are most likely to carry the bulk of cancer screening) is much higher. Once a lesion is palpated, documentation of the abnormality depends on the precision of a physician's description or a freehand diagram.

Several authors have proposed various types of devices mimicking palpation to detect tumors using different types of pressure sensors. For example Frei et al., U.S. Pat. No. 4,250,894, have proposed an instrument for breast examination that uses a plurality of spaced piezoelectric strips which are pressed into the body being examined by a pressure member which applies a given periodic or steady stress to the tissue beneath the strips.

Another approach to evaluate the elasticity of the tissues uses indirect means, such as conventional imaging modalities (ultrasound or MRI) which are capable of detecting motion of a tissue subjected to an external force. One approach attempts to determine the relative stiffness or elasticity of tissue by applying ultrasound imaging techniques while vibrating the tissue at low frequencies. See, e.g., J. J. Parker et al., U.S. Pat. No. 5,099,848; R. M. Learner et al., *Sono-Elasticity: Medical Elasticity Images Derived From Ultrasound Signals in Mechanically Vibrated Targets*, Acoustical Imaging, Vol. 16, 317 (1988); T. A. Krouskop et al., *A Pulsed Doppler Ultrasonic System for Making Non-Invasive Measurement of Mechanical Properties of Soft Tissue*, 24 J. Rehab. Res. Dev. Vol. 24, 1 (1987); Y. Yamakoshi et al., *Ultrasonic Imaging of Internal Vibration of Soft Tissue Under Forced Vibration*, IEEE Transactions on Ultrasonics Ferroelectrics, and Frequency Control, Vol. 7, No. 2, Page 45 (1990).

Sarvazyan et al., have developed a device for elasticity imaging of the prostate using an ultrasonic transrectal probe (U.S. Pat. No. 5,265,612). This device enables physicians to quantitatively and objectively characterize elasticity moduli of prostate tissues. The elasticity characterization and imaging is achieved by evaluating the pattern of the internal strain in the prostate and surrounding tissues using conventional transrectal ultrasonography. The pattern of internal strain is obtained by ultrasonically imaging the prostate at two levels of its deformation. The deformation is provided by changing the pressure in the fluid filling the sheath surrounding the transrectal probe. In addition to elasticity, other tumor parameters reflecting the stage of its development include the geometrical parameters of the tumor, such as its volume or diameter. Lacoste et al., U.S. Pat. No. 5,178,148, have disclosed a method of determining the volume of a tumor or gland, particularly the prostate, using an endocavity detector probe, in particular, a transrectal probe.

It has been described that the combination of palpation and detection by using prostate specific antigen (PSA) almost doubles the cancer detection rate, see Catalona et al., *A Multicenter Evaluation of PSA and Digital Rectal Examination (DRE) for Early Detection of Prostate Cancer in 6,374 Volunteers*, J Urol, Vol. 149 (Suppl), p. 412 (1993). The combined method is recommended by the American Urological Association and American Cancer Society, and was recently approved by FDA for screening patients between ages of 50 and 75 years old. It was demonstrated that a combined-modality approach to prostate cancer detection yields high levels of early detection with infrequent adverse outcomes, since palpation detects cancer that would otherwise be missed by PSA measurements.

It is desirable to provide an improved method and device for palpation and mechanical imaging of the prostate.

SUMMARY OF THE INVENTION

The present invention relates to a method for mechanically imaging the prostate with a prostate examination device and to the prostate examination device. In the method, position data and pressure response data are acquired along a predetermined pattern of trajectories overlaying the prostate by periodic pressing or sliding of a pressure sensor assembly attached to a probe against the prostate. A pattern of pressure responses and pressure gradient responses are determined and used for generating a mechanical image of the prostate. The predetermined trajectories provide efficient examination of the prostate.

In a preferred embodiment, the prostate examination device comprises a probe sized to fit within the rectum and having a head connected by a shaft to a handle. A support is connected to the probe for providing a point of rest for the shaft during the prostate examination. A pressure sensor assembly is coupled to the head for generating pressure signals in response to forces imposed on the pressure sensor assembly as the pressure sensor assembly is pressed against and moved over the prostate. A positioning system is coupled to the support and probe for determining position data of said pressure sensor assembly during prostate examination. An electronic unit receives the pressure data from the pressure sensor assembly and the position data from the positioning system and determines a structure of the prostate.

The invention will be more fully described by reference to the following drawings.

DETAILED DESCRIPTION

Figure 1:
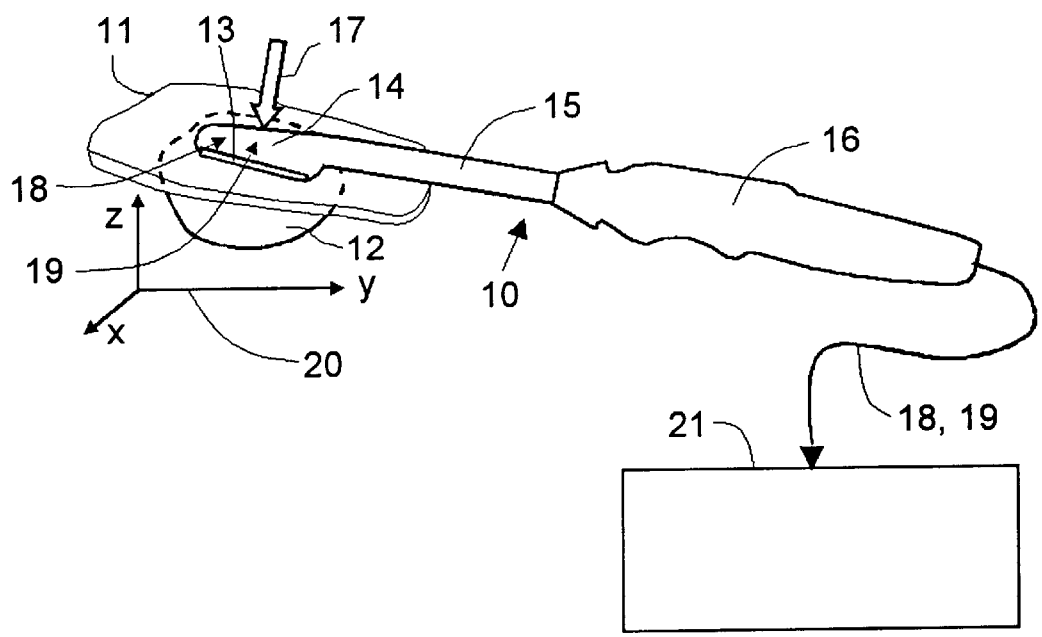
FIG. 1 is a perspective view illustrating the relationship of a probe, rectal wall and prostate during prostate examination.

Reference will now be made in greater detail to a preferred embodiment of the invention, an example of which is illustrated in the accompanying drawings. Wherever possible, the same reference numerals will be used throughout the drawings and the description to refer to the same or like parts.

The method for transrectal imaging of the prostate using the present invention is based on the technology of medical imaging described in U.S. Pat. No. 5,524,636, which is incorporated herein by reference. This method is referred to herein as Mechanical Imaging (MI). The essence of MI is the reconstruction of the internal structure of soft body tissues by measuring a surface stress pattern using a pressure sensing assembly. The pattern of mechanical stress and its changes as a function of applied pressure and time contain comprehensive information on the mechanical properties and geometry of the internal structures of the body tissues.

FIG. 1 schematically illustrates positioning of a transrectal probe used for measuring geometrical and mechanical parameters of the prostate during prostate examination. Probe 10 is sized to fit within the rectum. Probe 10 is positioned adjacent one side of rectal wall 11. Prostate 12 is positioned adjacent the other side of rectal wall 11. Probe 10 comprises pressure sensor assembly 13 mounted on head 14 for generating signals in response to forces imposed on pressure sensor assembly 13 as the pressure sensor assembly 13 is pressed against and moved over prostate 12. For example, pressure sensor assembly 13 can be formed of at least one pressure transducer. Shaft 15 connects head 14 to handle 16.

During prostate examination, in accordance with the present invention, probe 10 is inserted into the rectum and manipulated within the rectum using handle 16. In essence, head 14 is moved within the rectum and is pressed against rectum wall 11 along predetermined trajectories to palpate prostate 12 as shown by arrow 17. Aternatively, non-manual (e.g., computer driven) operation of the probe can be used to manipulate probe 10 within the rectum. Measurements from pressure sensor assembly 13 form pressure data 18. Pressure sensor assembly 13 can be mounted on a variety of devices (e.g., electromechanical or piezoelectric) designed to provide automatic operation of the pressure of pressure sensor assembly 13 against the prostate 12. Probe 10 can also include means for measuring the position and orientation of the probe, thereby determining position data 19 of the position and orientation of pressure sensor assembly 13 in coordinate system 20 referencing the human body. Thereafter, force sensor data 18 and position data 19 can be used in means for mechanical imaging of the prostate 21 to generate mechanical imaging results, as described in more detail below.

Figure 2A:
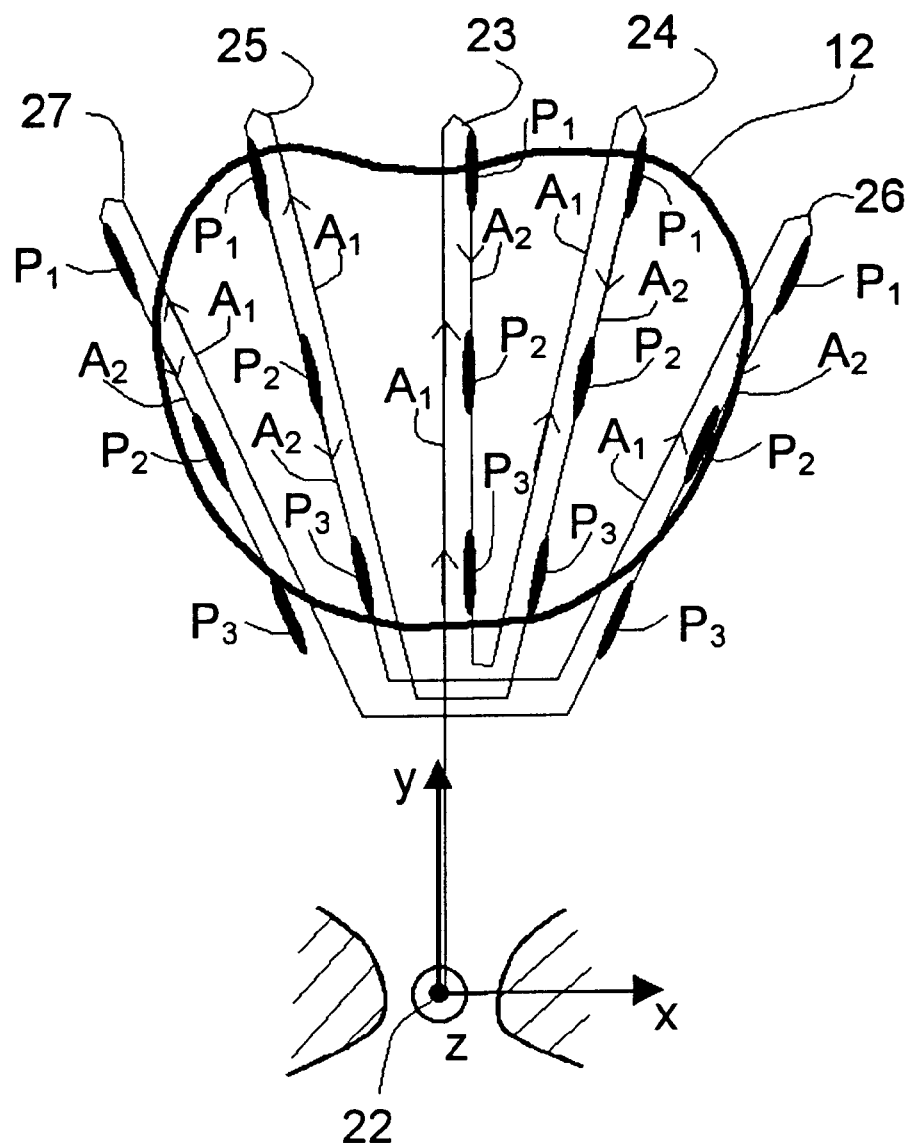
FIG. 2A is a schematic diagram of trajectories to be followed by a head of the probe during prostate examination while periodically pressing the probe against the prostate at the regions shown by a region of a thickened line in accordance with an embodiment of the method of the present invention.

Referring to FIG. 2A trajectories for moving and pressing pressure sensor assembly 13 during prostate examination are shown. Trajectories 23–27 are sequentially followed for moving probe 10 radially from sphincter 22. First, head 14 of probe 10 is moved along trajectory 23 in the direction of arrow $A_1$ away from sphincter 22 without pressing against prostate 12 in order to minimize displacement of the prostate. Second, head 14 is moved along the same trajectory 23 in the direction of arrow $A_2$ toward sphincter 22 with periodical pressing against prostate 12 at points $P_1$–$P_3$ positioned on trajectory 23, as shown by regions on the trajectory having a thickened line. A similar procedure is repeated along each trajectory 24–27 to provide pressure data 18 for mechanical imaging of prostate 12.

Figure 2B:
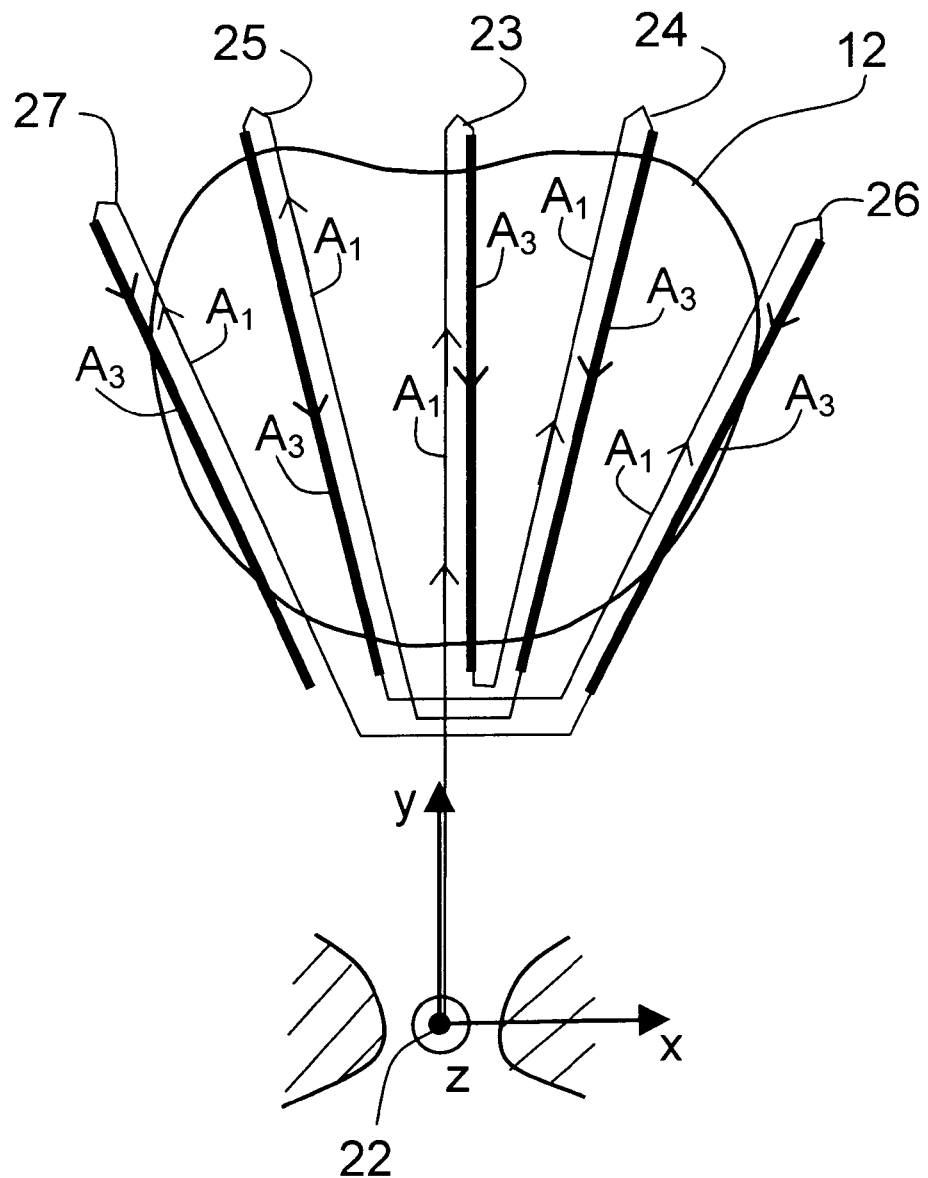
FIG. 2B is a schematic diagram of trajectories to be followed by a head of the probe during prostate examination while constantly pressing the probe against the prostate with sliding at the regions shown by thickened lines.

An alternative type of application of pressure by pressure sensor assembly 13 along trajectories 23–27 is shown in FIG. 2B. Pressure sensor assembly 13 is moved along trajectories 23–27 in the direction of arrow $A_1$ away from sphincter 22 without pressing against prostate 12. Pressure sensor assembly 13 slides along trajectories 23–27 in the direction of arrow $A_3$ towards sphincter 22 while applying constant pressure by pressing against prostate 12. This type of palpation provides distinct prostate geometrical features along the motion trajectory and minimizes possible prostate displacement laterally during examination.

Figure 3A:
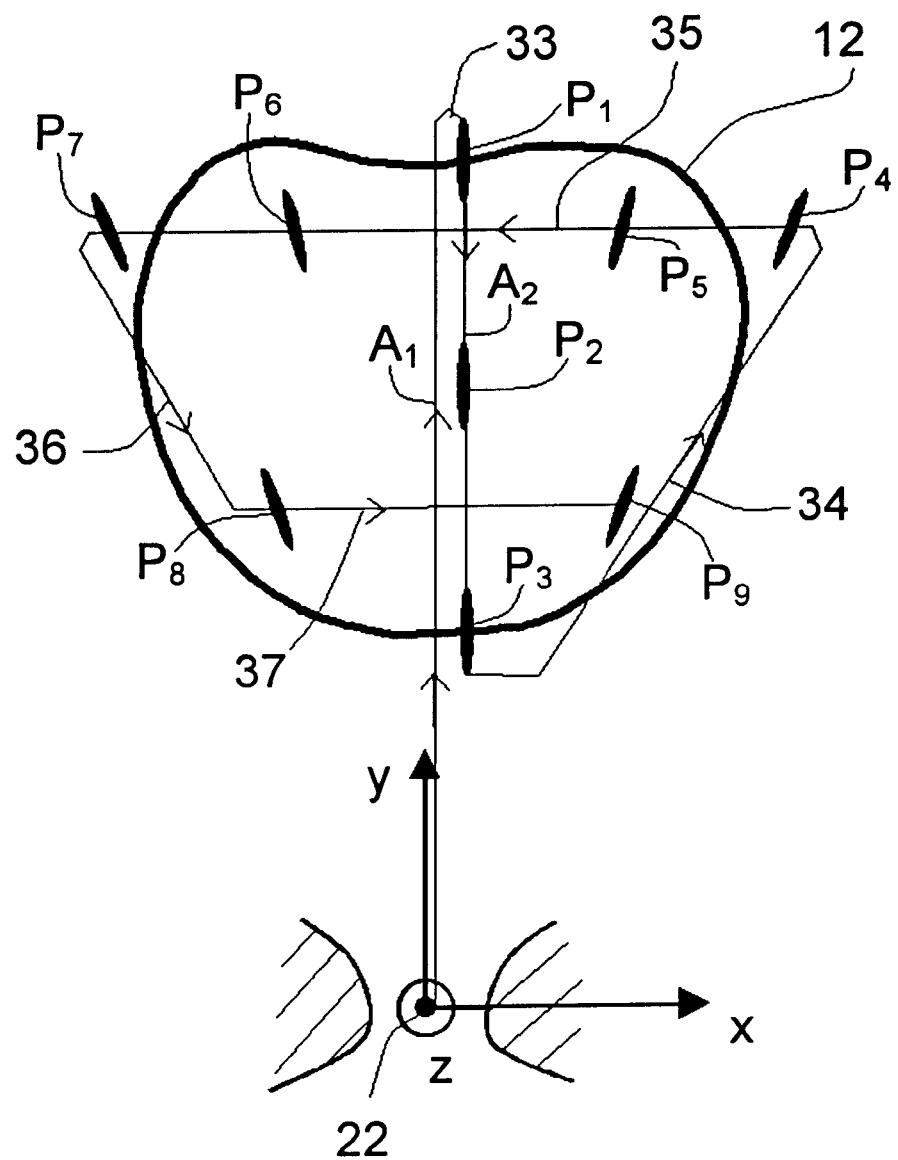
FIG. 3A is a schematic diagram of an alternative trajectory to be followed by a head of the probe during prostate examination while periodically pressing the probe against the prostate at the regions shown by dark sports in accordance with an embodiment of the method of the present invention.

FIG. 3A illustrates another pattern of trajectories for moving and pressing pressure sensor assembly 13 during prostate examination. First, pressure sensor assembly 13 is moved along trajectory 33 in the direction of arrow $A_1$ away from sphincter 22. Second, pressure sensor assembly 13 is moved along trajectory 33 in the direction of arrow $A_2$ towards sphincter 22 with periodical pressing against prostate 12 at points $P_1$–$P_3$ to provide prostate geometrical features along axis Y. Third, pressure sensor assembly 13 is moved along trajectory 34 for radially moving away from sphincter 22 without pressing against prostate 12. Fourth, pressure sensor assembly 13 is moved along trajectory 35 to laterally pass from one side of an upper region of prostate 12 to the other with pressing at points $P_4$–$P_7$. Fifth, pressure sensor assembly 13 is moved along trajectory 36 for radially moving toward sphincter 22 to a lower region of prostate 12 without pressing. Sixth, pressure sensor assembly 13 is moved along trajectory 37 to laterally pass from one side of the lower region of prostate 12 to the other with pressing at points $P_8$–$P_9$ against prostate 12. Periodic pressing along trajectories 35 and 37 provide prostate geometrical features along axis X. The second pattern of trajectories provides an improved time duration for prostate examination, for example the examination can be performed in around 20 seconds. It will be appreciated that the pattern of trajectories and points for applying pressure against prostate 12 can be altered to provide a varied examination procedure.

Figure 3B:
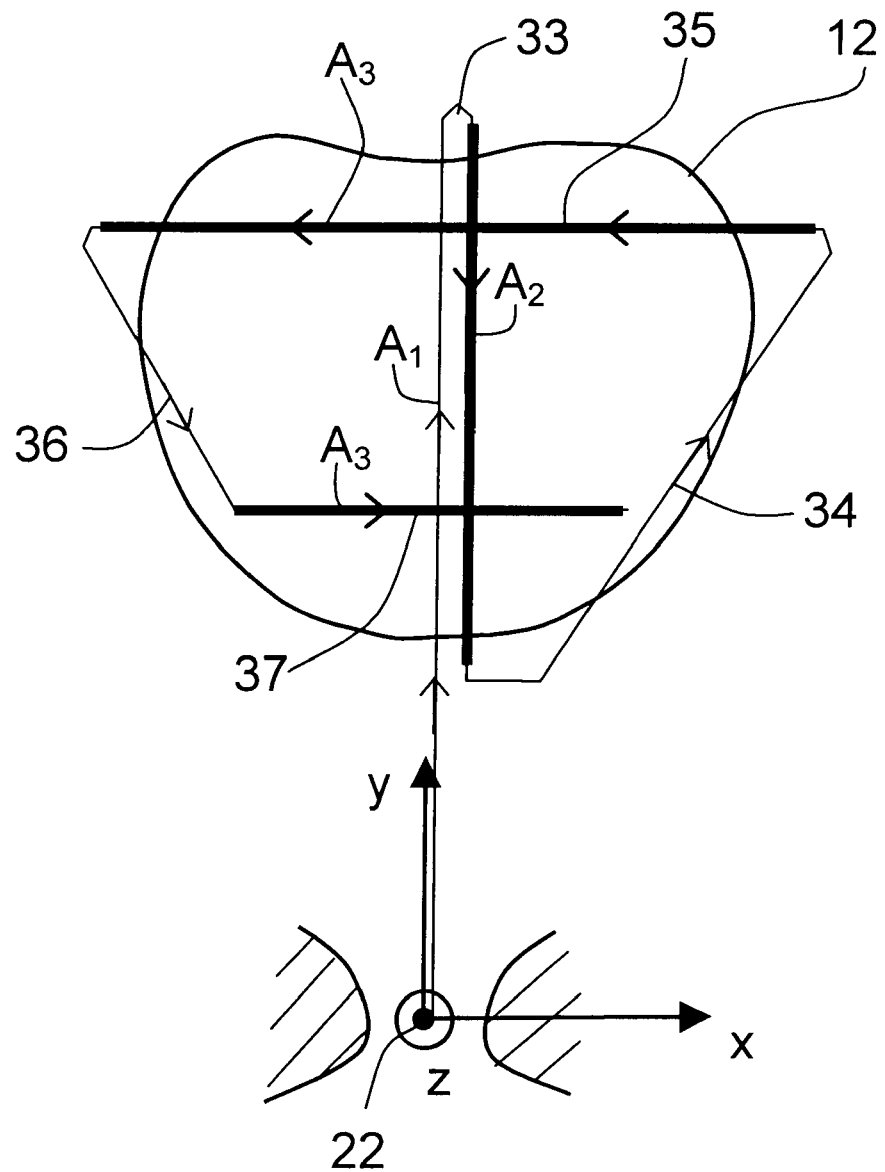
FIG. 3B is a schematic diagram of an alternative trajectory to be followed by a head of the probe during prostate examination while constantly pressing the probe against the prostate with sliding at the regions shown by thicken lines.

An alternative type of application of pressure by pressure sensor assembly 13 along the trajectories 33–37 is shown in FIG. 3B. Pressure sensor assembly 13 slides along trajectories 35 and 37 in the direction of arrow $A_3$ while applying constant pressure against prostate 12. This type of palpation provides distinct prostate geometrical features along the motion trajectory and minimizes possible prostate displacement.

Figure 4A:
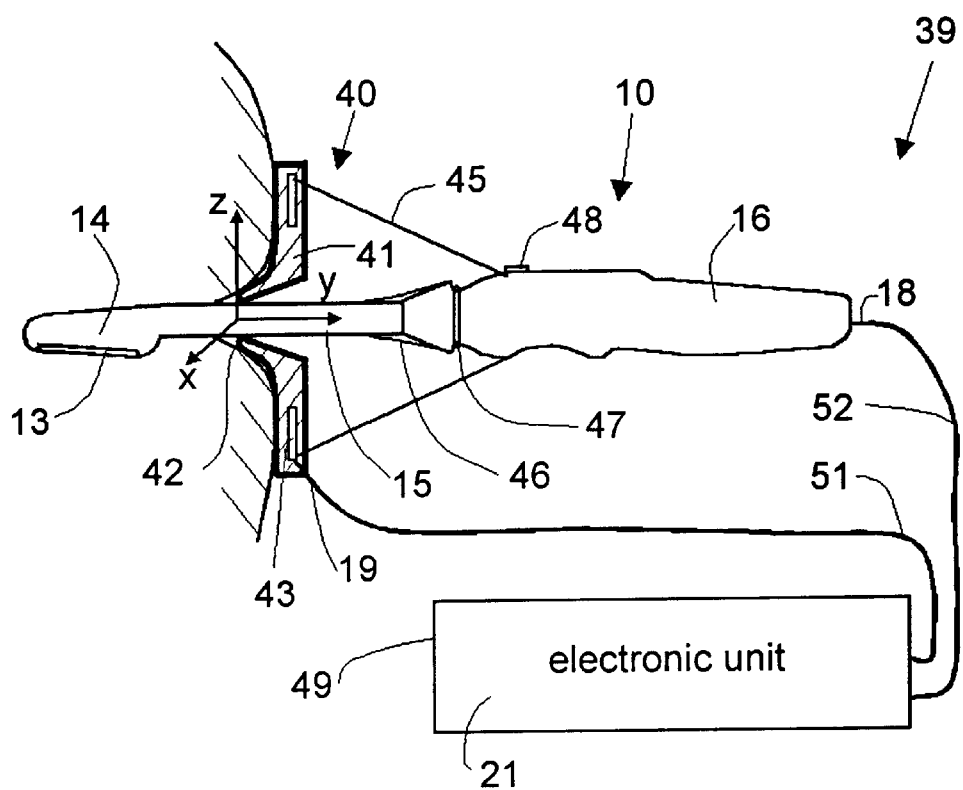
FIG. 4A is a cross-sectional side view of a mechanical positioning system used with the probe during prostate examination.
Figure 4B:
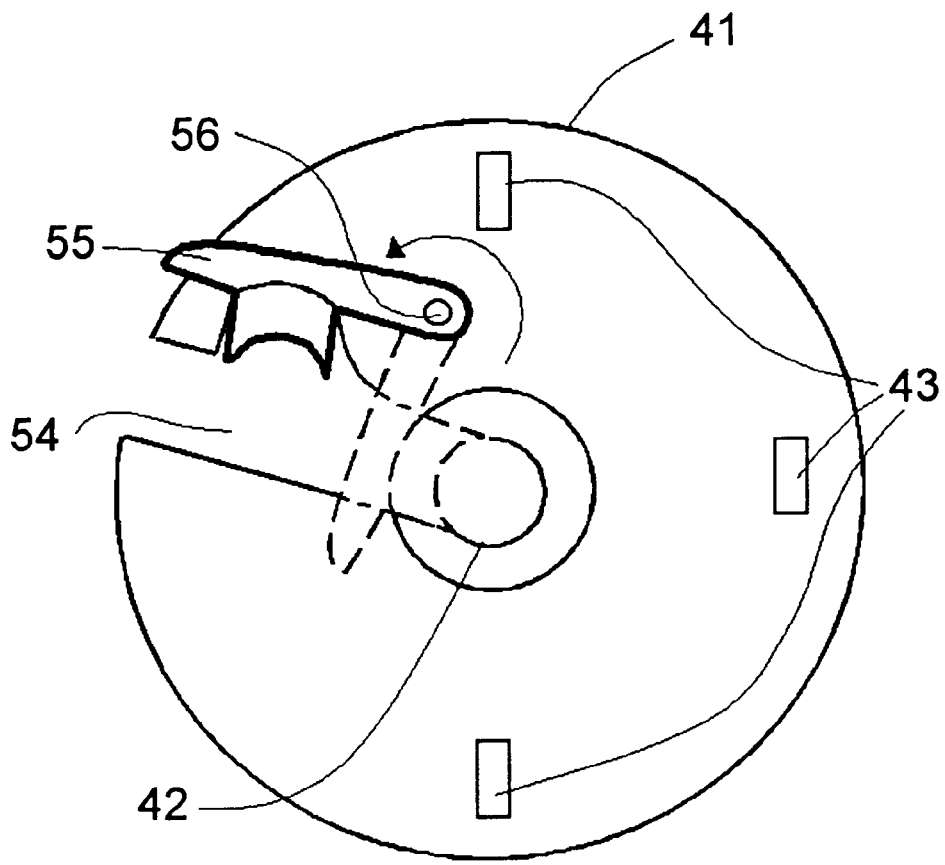
FIG. 4B is an end view of a support with a lock mechanism of the mechanical positioning system of FIG. 4A.

Referring to FIGS. 4A and 4B, prostrate examination device 39 preferably comprises probe 10 and positioning system 40. Positioning system 40 comprises support 41 mechanically connected to handle 16. Shaft 15 of probe 10 is received in aperture 42 of support 41. Support 41 provides a point of rest for shaft 15 against the buttocks of the patient during the prostate examination. Positioning system 40 also includes a plurality of transducer elements 43 for generating signals in response to movements of handle 16 relative to support 41. Accordingly, transducer elements 43 generate position data 19. For example, three transducer elements 43 can be attached to support 41. Each transducer element 43 can be formed of a load cell coupled to support 41 and mechanically connected to handle 16 by elastic thread 45.

Preferably, thin elastic cover 46 covers head 14 and shaft 15. Thin elastic cover 46 is held by fixing ring 47 to handle 16. Thin elastic cover 46 can be removed from shaft 15 after use and discarded before the next use. Thereafter, a new thin elastic cover 46 can be placed over shaft 15 before the next use for providing improved hygienics of the prostate examination.

Slot 54 is formed in support 41, as shown in FIG. 4B. Revolving locker 55 rotates around axis 56 for opening and closing slot 54. Revolving locker 55 is shown in open position by solid line and in the closed position by dotted line. In the closed position, probe 10 is locked in a working position. Revolving locker functions to make head 14 and shaft 15 of probe 10 available for replacing of thin elastic cover 46 before the next use of probe 10.

Figure 5:
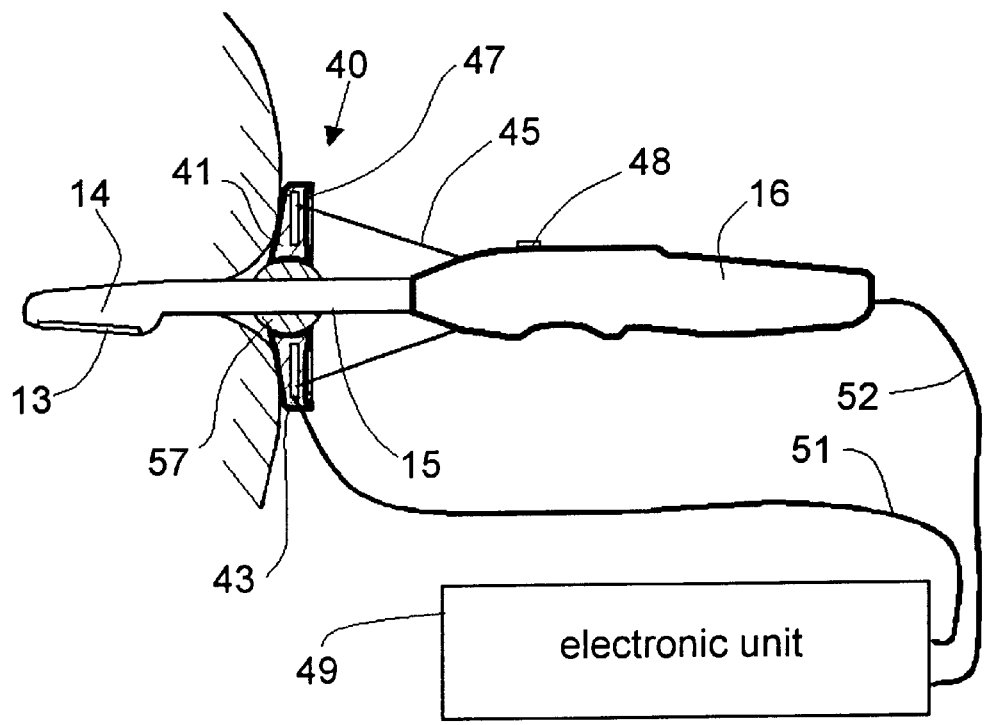
FIG. 5 is a cross-sectional side view of an alternative mechanical positioning system having ball and socket joint.

FIG. 5 illustrates an alternative mechanical positioning system 40 coupling support 41 to ball and socket joint 57. Ball and socket joint 57 provides rotational motion of shaft 15. Positioning system 40 measures rotation of shaft 15 and displacement of shaft 15 from support 41 during prostate examination.

Figure 6:
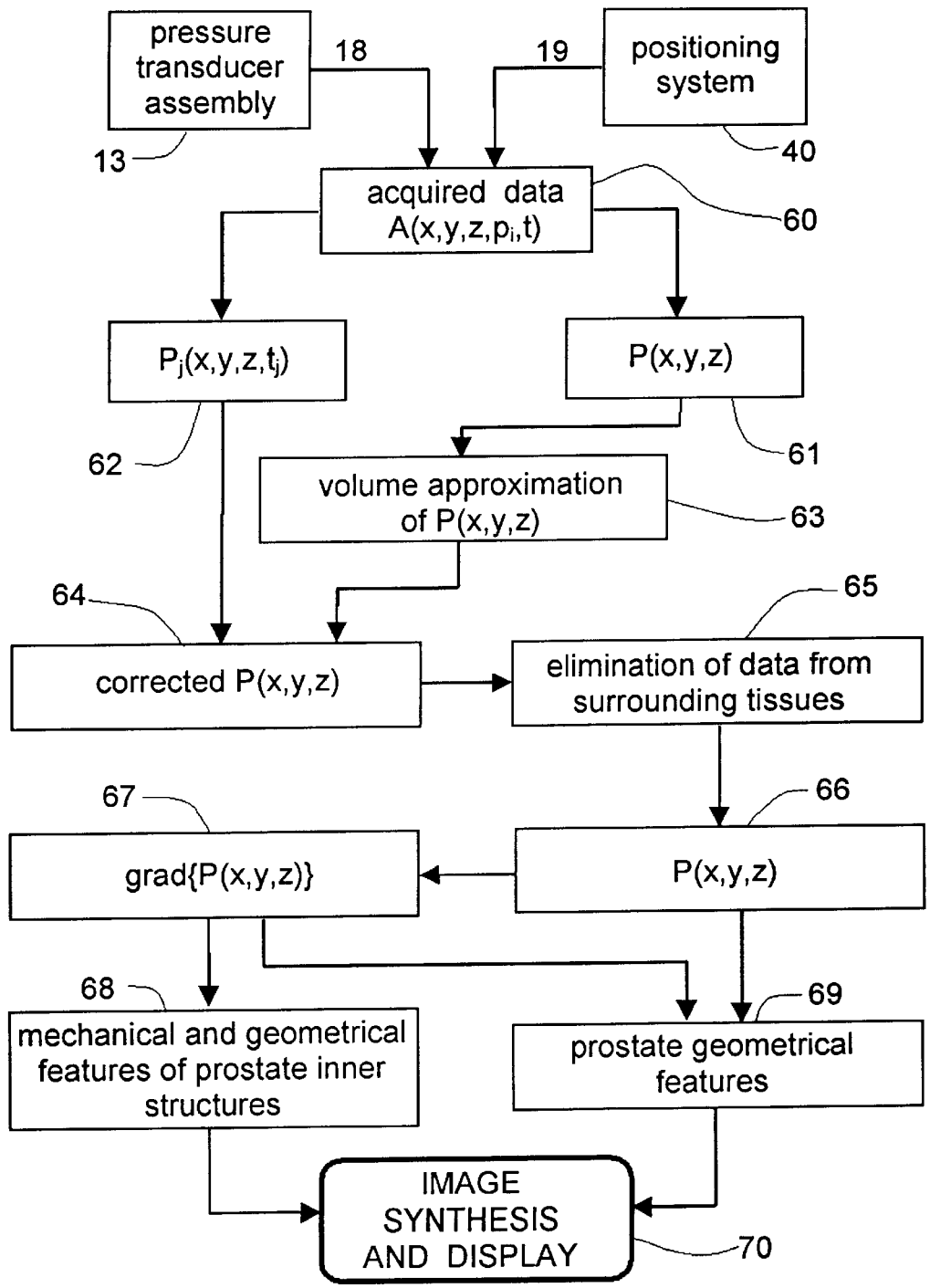
FIG. 6 shows a flow chart representative of an algorithm for determining diagnostic information from palpation data and position data to be used in mechanical imaging.

FIG. 6 is a flow chart of the preferred method of synthesizing a three-dimensional prostate image. Pressure data 18 from pressure sensor assembly 13 and position data 19 from positioning system 40 are acquired in real-time. Position data 19 represents relative coordinates of some fixed point of the probe 10 represented by (x, y, z) at time t with the origin being sphincter 22. Analog signals representing pressure measured from all the pressure transducers of pressure sensor assembly 13 at time t form pressure data 18 represented by $(p_i,t)$. In block 60, pressure data 18 and position data 19 are combined over time into acquired data represented by $A(x,y,z,p_i,t)$.

Using force calibration data and knowing the position for each pressure transducer relative to the fixed point of the probe 10, the acquired data is combined over a period of time to form pressure data file $P(x,y,z)$ in block 61. A plurality of data subsets $P_j(x,y,z,t_j)$ are formed in block 62 from the acquired data.

In block 63, data file $P(x,y,z)$ is processed by one of the known volume approximation methods, as described for example by Y. L. Lute, *Mathematical functions and their approximations*, Academic Press Inc., New York (1975), to determine geometry of the prostate. In block 64, corrected data $P(x,y,z)$ is determined for correcting displacement and shifting of the prostate during examination and correcting noise of various origins. The noise originates from force and position measurement error and from artifacts related to tissue movement (movement of the prostate, movement of the patient). Pressure field data is calculated by processing the transformed data to minimize noise and extract the 3D spatial distribution of pressure approximating ideal conditions of measurement. Data related to tissue surrounding prostate 12 are eliminated in block 65 from corrected pressure data file $P(x,y,z)$. It may be done for example by removing points with negative value $\partial P(x,y,z)/\partial x$ at the left of the prostate center and positive value $\partial P(x,y,z)/\partial x$ at the right of the prostate center.

A pattern of pressure responses of the prostate represented by $P(x,y,z)$ is determined in block 66. In block 67, a pattern of pressure gradient responses represented by grad$\{P(x,y,z)\}$ is determined from the pattern of pressure responses of the prostate. Different methods may be used to determine the pressure gradient responses grad{P(x,y,z)}, one of which is calculating partial derivatives for the pattern of pressure responses of the prostate. In block 68, mechanical and geometrical features of the prostate inner structures are determined from the pressure gradient responses. In block 69, the pattern of pressure responses of the prostate P(x,y,z) is corrected subject to distortions from the stiffer tissue inside the prostate which are revealed in the pressure gradient responses to determine prostate geometrical features. In block 70, a prostate image is synthesized from data generated in block 68 and data generated in block 69. Having approximated (above) smooth surfaces of equal pressure, one can calculate geometrical parameters and hardness of the prostate. The surface of the examined prostate can be obtained by choosing a level of force corresponding to deformation of the rectal wall that permits the sensors to press against the prostate surface. From the pressure gradients, information on the prostate tissue hardness can be generated.

The synthesized image can be displayed on a computer display. An average level of pressure applied to pressure sensor assembly 13, the position, real trajectory of pressure sensor assembly 13 and the predetermined pattern of trajectories for movement of the probe can be indicated in real-time in a plane projection over the prostate image on the same computer display beginning from sphincter 22. Points of pressing on the trajectories can also be displayed.

Figure 7:
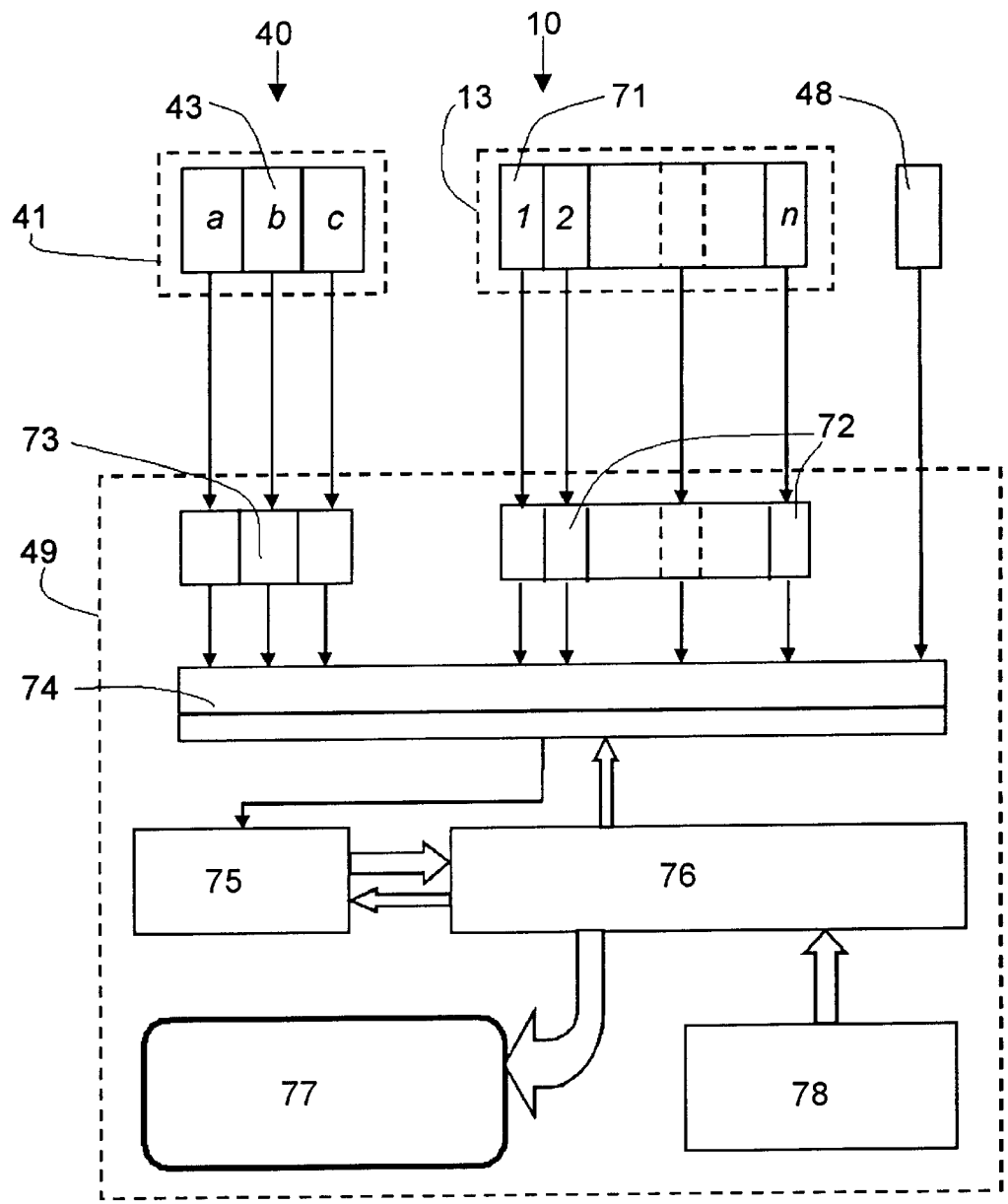
FIG. 7 is a schematic diagram of an electronic unit for providing acquisition, processing and displaying of mechanical imaging data from the probe and mechanical positioning system shown in FIG. 4A.

FIG. 7 illustrates a schematic diagram of a preferred embodiment of electronic unit 49 coupled to probe 10 and positioning system 40. A plurality of transducer elements 71 form pressure sensor assembly 13 of probe 10. A pressure sensing circuit is formed of a plurality of amplifiers 72 to amplify respective signals generated by pressure transducer elements 71, for detecting the force imposed on each transducer element 71 of pressure sensor assembly 13. A plurality of amplifiers 73 amplify signals generated by respective load cells 43, for detecting the position of each load cell 43 of positioning system 40.

The amplified signals from amplifiers 72 and 73 are applied to multiplexer 74. Control signals from button 48 are also applied to multiplexer 74. Multiplexed signals are converted to digital signals by analog-to-digital converter 75 and fed to processor 76. Processor 76 is used for signal processing to calculate the position of each pressure sensing transducer 71 during prostate examination, to approximate and correct mechanical imaging of the prostate and surrounding tissues, for separation and analysis of the prostate mechanical imaging, for determining the prostate geometrical features and mechanical features of prostate inner structures such as lesions, nodules, stiffer tissue and the like, and for prostate image synthesis, as described in the method illustrated in FIG. 6. Display device 77 is connected to processor 76, thereby displaying the prostate examination process and the results of the examination. Control unit 78 is connected to processor 76 for controlling the prostate examination process, data analysis and data display. Processor 76 communicates with analog-to-digital converter 75 and multiplexer 74 for sending data and control signals.

Figure 8:
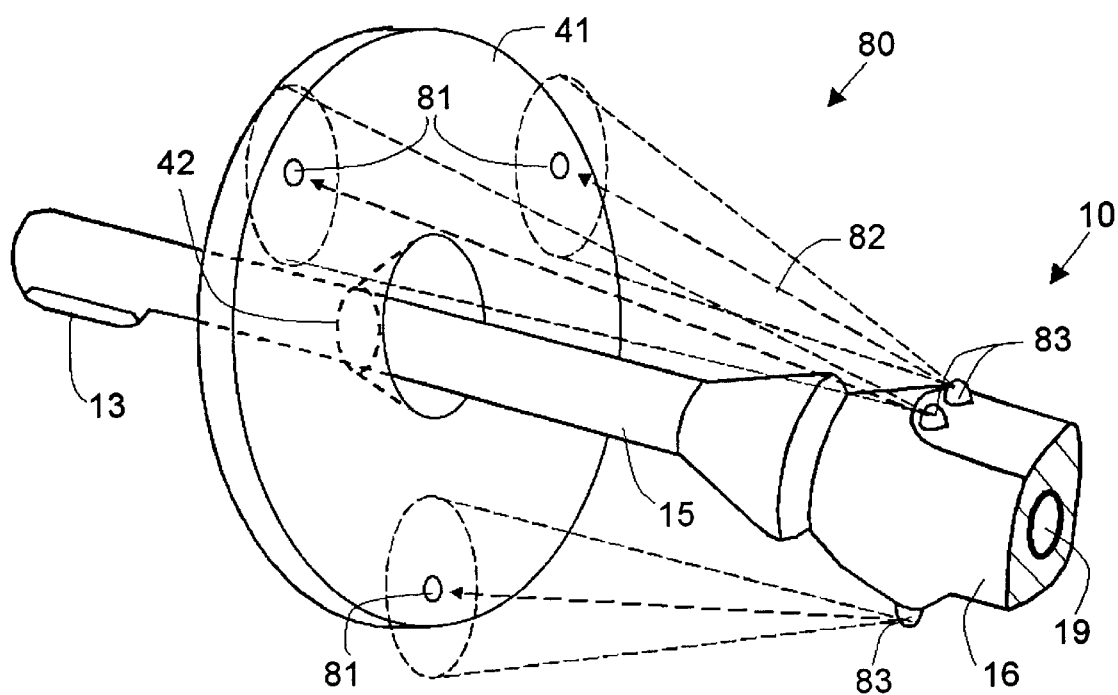
FIG. 8 is a perspective view of an alternative positioning system including an optical system.

FIG. 8 illustrates an alternate embodiment of mechanical positioning system 40 as an optical positioning system 80 coupled to support 41 and handle 16 for determining real-time position data 19 of pressure sensor assembly 13 during prostate examination. Optical positioning system 80 comprises a plurality of optical devices 81 coupled to support 41 and a plurality of optical devices 83 coupled to handle 16 for generating signals in response to movements of handle 16 relative to the support 41. For example, optical positioning system 80 can comprise an opto-electronic pair, in which optical device 81 can be a photodiode and optical device 83 can be a light diode. Light beams 82 are emitted from light diode 83 and are received at photodiode 81. Frequency modulation can be used to provide different frequencies for each opto-electronic pair of optical devices 81 and 83. In this embodiment, electronic unit 49 includes a distance sensing circuit, responsive to the signals generated by optical devices 81 and 83, for detecting the position of handle 16 relative to the support 41. For example, the distance sensing circuit can be a conventional circuit for determining the distance between optical device 81 and optical device 83 from the intensity of light received at optical device 81.

Figure 9:
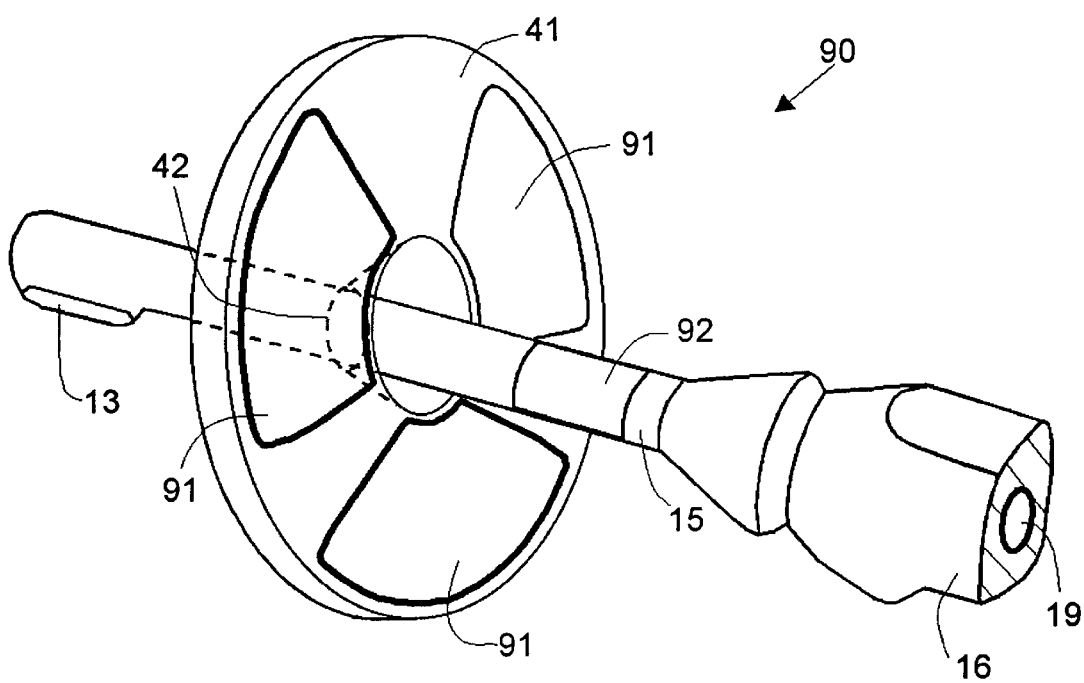
FIG. 9 is a perspective view of an alternative positioning system including an electrical capacitance sensor based system.

FIG. 9 illustrates another alternative embodiment of mechanical positioning system 40 as an electrical capacitance positioning system 90. Electrical capacitance system 90 is coupled to support 41 and shaft 15 for determining real-time position data 19 of pressure sensor assembly 13 during prostate examination. Electrical capacitance positioning system 90 includes a plurality of variable-capacitance transducers for generating signals in response to movements of handle 16 relative to support 41. Preferably, the capacitance transducer is formed of a plurality of electrodes 91 connected to support 41 and an electrode 92 connected to shaft 15. In this embodiment, electronic unit 49 includes a distance sensing circuit, responsive to the signals generated by electrodes 91 and electrode 92 for determining the distance between these electrodes, thereby determining the position of shaft 15 relative to support 41. For example, the distance sensing circuit can be a conventional circuit for determining the distance between electrodes 91 and electrode 92 from the amplitude of the signal generated by electrode 91 and received at electrode 92.

Figure 10:
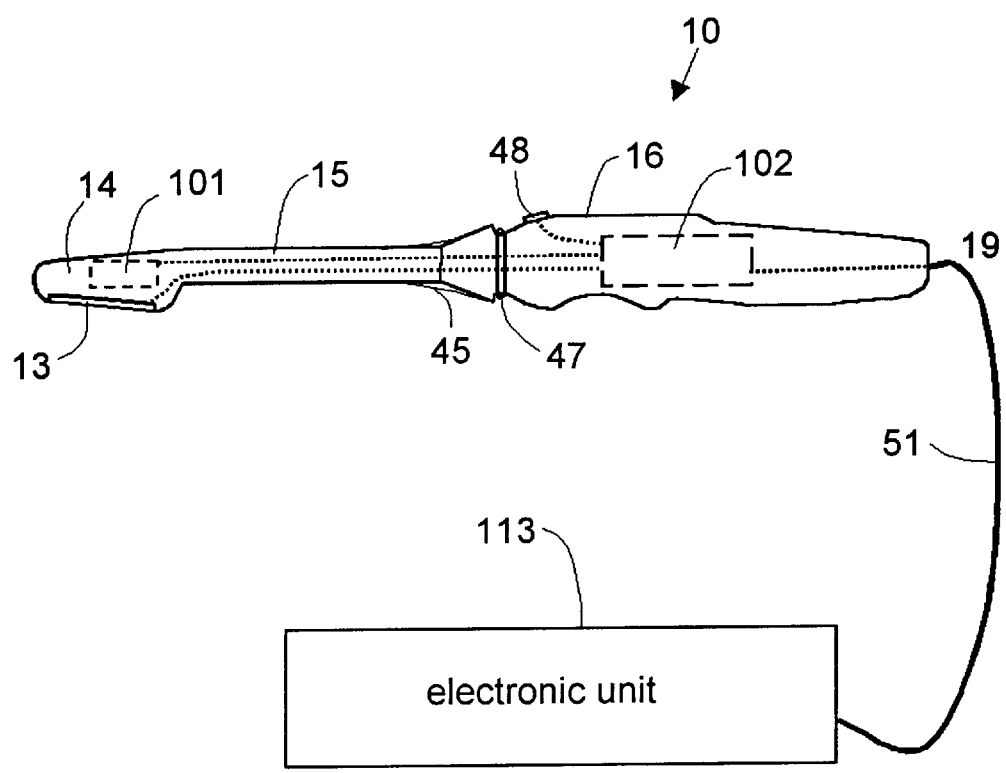
FIG. 10 is a schematic diagram of another alternative embodiment of the positioning system including an accelerometer based positioning system and probe.

FIG. 10 is an alternative embodiment of mechanical positioning system 40 in which positioning system 101 and electronic unit 102 are positioned within probe 10. Connection 51 connects electronic unit 102 to remote electronic unit 113. Positioning system 101 determines real-time position data 19 of pressure sensor assembly 13 during prostate examination. Preferably, positioning system 101 can be located in head 14 or in handle 16 of probe 10. Electronic unit 102 preferably can be fitted in handle 14. Positioning system 101 can be formed of a triaxial accelerometer.

Figure 11:
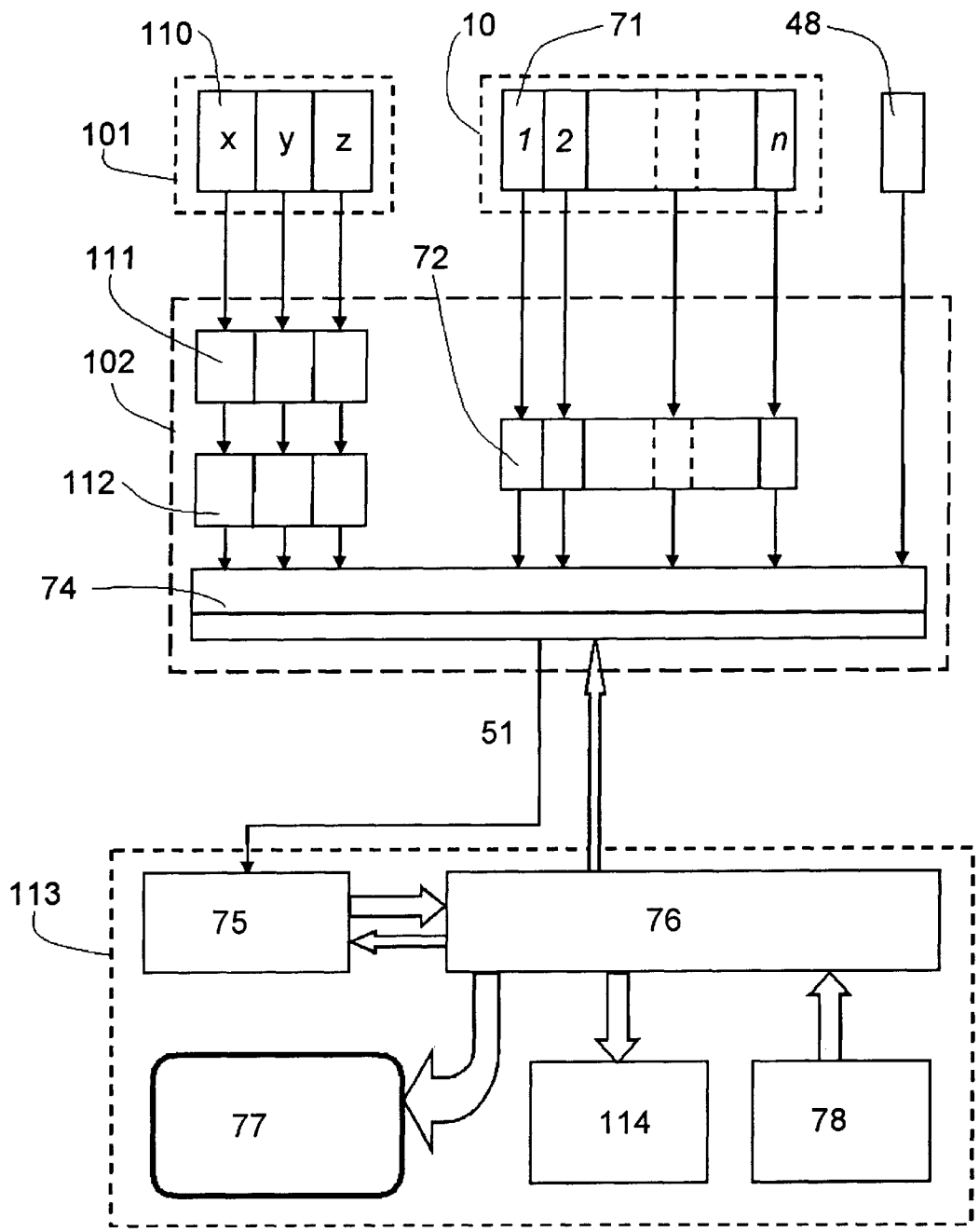
FIG. 11 is a schematic diagram of an electronic unit for providing data acquisition, processing and displaying from the positioning system shown in FIG. 10.

FIG. 11 shows a schematic diagram of electronic unit 102 connected to a remote electronic unit 113. Electronic unit 102 provides data acquisition of pressure data 18 and position data 19. Remote unit 113 provides processing and displaying of pressure data 18 and position data 19 from positioning system 101. Positioning system 101 is formed of triaxial accelerometer 110. Amplifiers 111 are positioned in electronic unit 102. Amplifiers 111 amplify signals generated by accelerometers 110. A plurality of analog integrating circuits 112 receive the amplified signals and determine relative 3D motion of probe 10 during the prostate examination. Signals from analog integrating circuits 112 and amplifiers 72, and button 48 are applied to multiplexer 74. Multiplexed signals are received over connection 51 at analog-to-digital converter 75 positioned in remote electronic circuit 113. Remote electronic circuit 113 also includes processor 76, display device 77 and control unit 78. Processor 76 communicates with analog-to-digital converter 75 and multiplexer 74 for sending data and control signals. A storage device 114 can be used in remote electronic unit 113 for storing the results of the prostate examination generated by processor 76.

Figure 12:
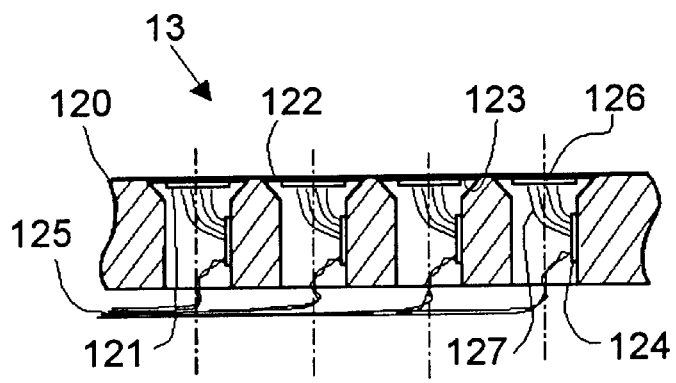
FIG. 12 is a cross-sectional side view of a pressure sensor assembly including a diaphragm pressure sensor assembly.

FIG. 12 is a cross sectional diagram of an embodiment of pressure sensor assembly 13. A plurality of flexing diaphragms 122 are located on bearing 120. Bearing 120 can be positioned at the base of head 14 or can be positioned at any surface of head 14. Bottom side 123 of flexing diaphragms 122 is bonded to a fully active or half active Wheatstone Bridge 126 having strain gages 121. Alternatively, Wheatstone Bridge 126 can include semiconductor strain gages, diffused piezoresistive strain sensors, ion-implanted piezoresistive strain sensors, thin film piezoresistive strain sensors or epitaxial piezoresistive strain sensors or other conventional sensors. Wires 127 coupled to strain gages 121 are connected with electrical connector 124 to electrical wires 125. Electrical wires 125 can be connected to connection 52.

Figure 13:
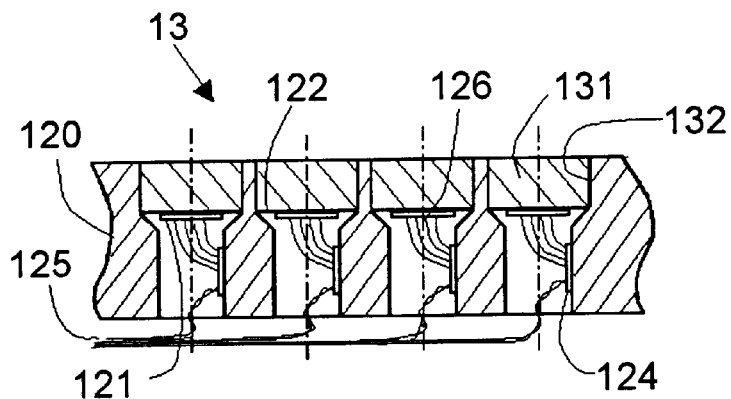
FIG. 13 is a cross-sectional side view of an alternative diaphragm pressure sensor assembly including a filled volume over the diaphragm.

FIG. 13 shows an alternative embodiment of pressure sensor assembly 13 in which flexing diaphragms 122 are positioned in respective cylinders 132. Each cylinder 132 is filled with an elastic material 131.

Figure 14:
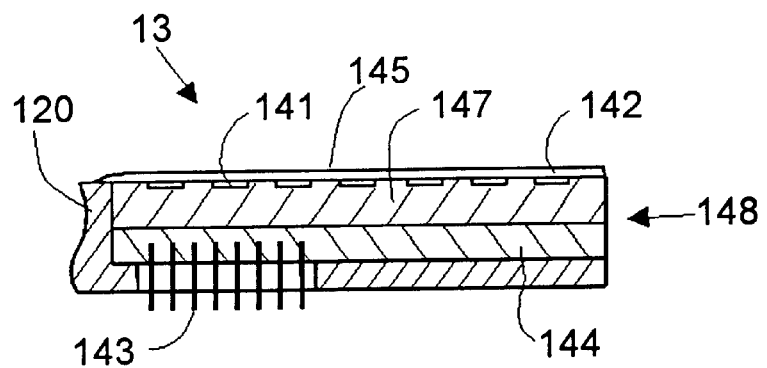
FIG. 14 is a cross-sectional side view of another alternative diaphragm pressure sensor assembly including a semiconductor chip.

FIG. 14 illustrates an alternative embodiment of pressure sensor assembly 13 formed of plurality of microfabricated pressure sensors 141 integrated into a monolithic sensor-circuit chip 148. Sensing surface 145 of pressure sensors 141 is covered with an elastic protective film 142. Monolithic sensor-circuit chip 148 is formed of semiconductor layer 147, oxide coating 144 and electrical connectors 143. Electrical connectors 143 can be connected to connection 52.

Figure 15A:
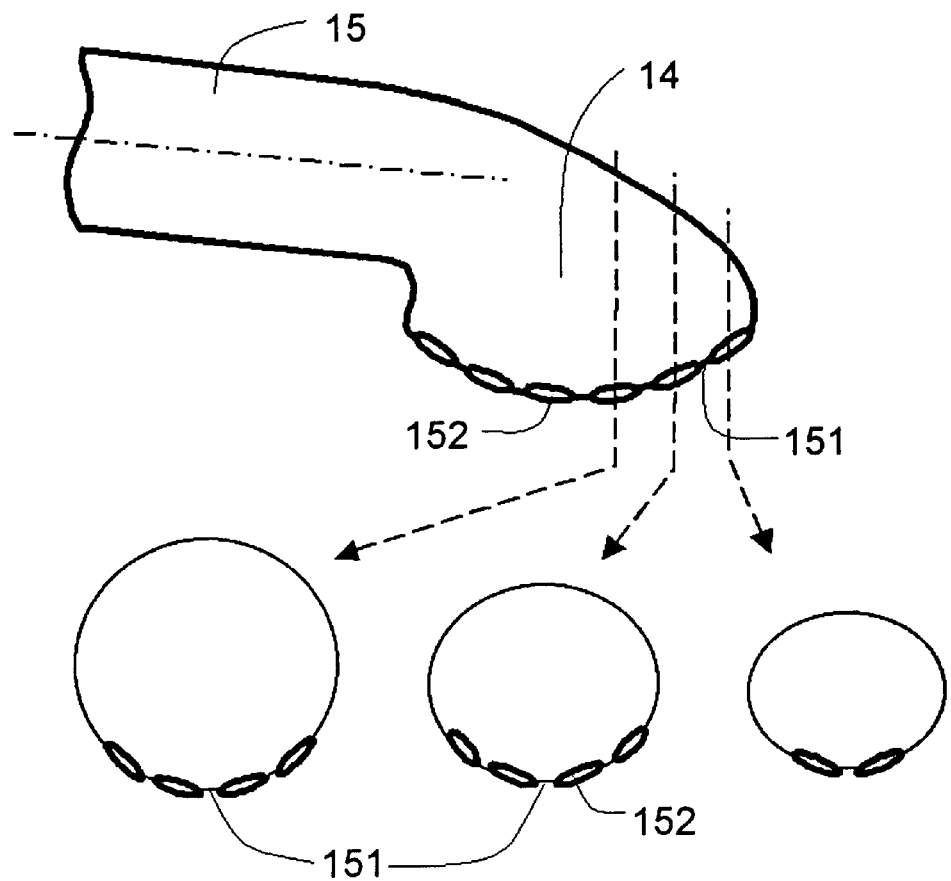
FIG. 15A is a side and cross-sectional view of the head of the probe having a biconvex shape and including a sensor assembly positioned on the head.
Figure 15B:
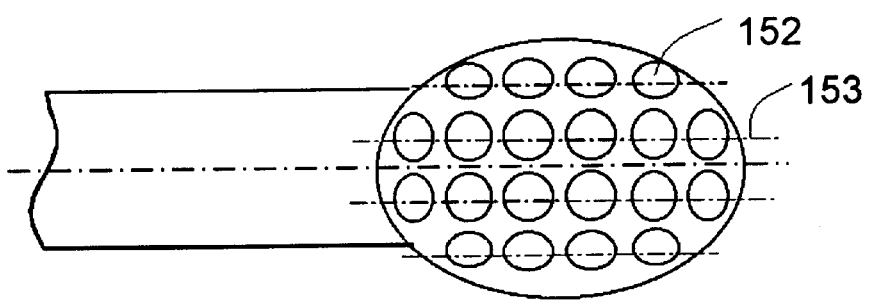
FIG. 15B is a bottom view of the head shown in FIG. 15A.

FIGS. 15A and 15B illustrate an embodiment of head 14 of probe 10. Head 14 is formed of surface 151. Preferably, surface 151 has a biconvex shape. A plurality of pressure sensors 152 are positioned along lines 153. Pressure sensors 152 provide palpation data 18. Alternatively, surface 151 can have a spherical shape or alternative geometric shapes which are sized to fit in the rectum.

Figure 16A:
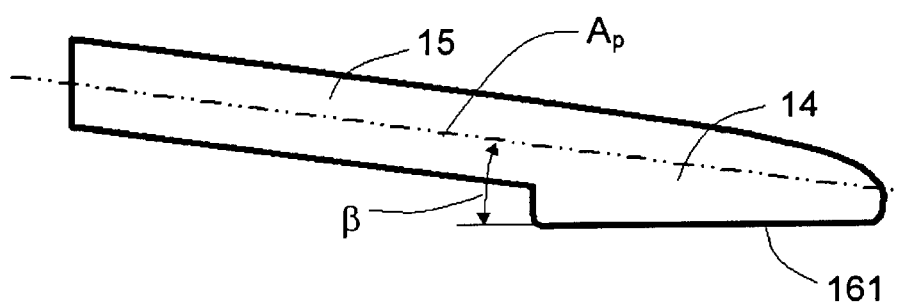
FIG. 16A is an elevational side view of an alternative head of the probe having a flat force sensing area and including a sensor assembly positioned on the head.
Figure 16B:
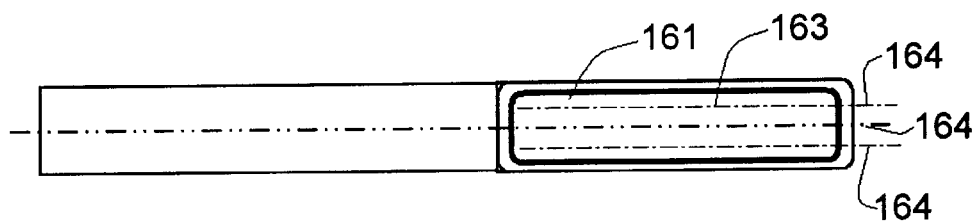
FIG. 16B is a bottom view of the head of the probe shown in 16A.

FIGS. 16A and 16B illustrate an alternative embodiment of head 14 of probe 10. Head 14 is formed of surface 161. Preferably, surface 161 is substantially flat. Surface 161 is formed at an angle β from the axis, $A_p$, of probe 10. For example, angle β can be about 6°. A plurality of pressure sensors 163 are positioned along lines 164. Pressure sensors 163 provide palpation data 18. Alternatively, surface 161 is concave or convex.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. A method for mechanically imaging a prostate comprising the steps of:
   acquiring position data and pressure response data of a pressure sensor assembly during movement of said pressure sensor assembly along predetermined trajectories overlaying said prostate;
   determining a plurality of positions and measured pressures of said pressure sensor assembly from said position data and said pressure response data;
   calculating a pattern of pressure responses and pressure gradient responses from the determined plurality of positions and measured pressures; and
   generating a mechanical image of the prostate from the calculated pressure responses and pressure gradient responses.

2. The method of claim 1 wherein said predetermined trajectories pass radially from the sphincter and said movement of said pressure sensor assembly along each of said trajectories away from the sphincter is performed without pressing of said pressure sensor assembly and said movement of said pressure sensor assembly toward the sphincter is performed with periodic pressing of said pressure sensor assembly against the prostate, thereby minimizing prostate displacement during prostate examination.

3. The method of claim 1 wherein said predetermined trajectories pass radially from the sphincter and said movement of said pressure sensor assembly along each of said trajectories away from the sphincter is performed without pressing of said pressure sensor assembly and said movement of said pressure sensor assembly toward the sphincter is performed under constant pressure with sliding of said pressure sensor assembly over the prostate in the rectum.

4. The method of claim 1 wherein said predetermined trajectories are formed of at least one radial trajectory passing radially from the sphincter and at least one lateral trajectory passing laterally from one side of the prostate to the other.

5. The method of claim 1 wherein said movement of said pressure sensor assembly along said predetermined trajectories is indicated in real-time during prostate examination on a display in a plane projection over said trajectories shown on the prostate image.

6. The method of claim 5 wherein an average level of pressure applied to said pressure sensor assembly is indicated on said display.

7. The method of claim 5 wherein said movement of said pressure sensor assembly along said predetermined trajectories is displayed beginning from the sphincter.

8. The method of claim 1 wherein said pressure sensor assembly comprises a plurality of pressure sensors and said step of determining a plurality of positions comprises:
   determining an origin of a coordinate system connected to the human body; and
   calculating the position of each of said pressure sensors in said coordinate system.

9. The method of claim 8 wherein said step of determining an origin of a coordinate system connected to the human body comprises the step of:
   calculating coordinates of the sphincter in a coordinate system connected to a positioning system.

10. The method of claim 1 wherein said pressure sensor assembly comprises a plurality of pressure sensors and said step of calculating a pattern of pressure responses comprises the step of:
    forming a data file containing pressure, position coordinates and time for all of said plurality of pressure sensors during prostate examination.

11. The method of claim 10 further comprising the step of eliminating data from tissue surrounding the prostate from said pattern of pressure responses to create a corrected pattern of pressure responses of the prostate.

12. The method of claim 1 wherein said step of calculating the pattern of pressure gradient responses comprises the step of:
    calculating partial derivatives of pressure for said pattern of pressure responses to determine size and position of stiffer tissue inside the examined prostate.

13. The method of claim 12, wherein said pattern of pressure responses of the prostate is corrected subject to distortion from tissue hardness variations inside prostate to determine prostate geometrical features.

14. A prostate examination device comprising:
    a probe sized to fit within the rectum and having a head connected by a shaft to a handle;

support means connected to said probe for providing a point of rest for said shaft during a prostate examination;

a pressure sensor assembly coupled to said head for generating signals in response to forces imposed on said pressure sensor assembly as said pressure sensor assembly is pressed against and moved over the prostate;

a positioning system coupled to said support means and probe for determining position data of said pressure sensor assembly during prostate examination; and an electronic unit for receiving said signals from said pressure sensor assembly and said position data from said positioning system, determining and displaying a structure of said prostate from said pressure sensor signals and said position data.

15. The prostate examination device of claim 14 wherein said positioning system comprises:
a plurality of mechanical transducer elements for generating signals in response to movements of said handle relative to said support means.

16. The prostate examination device of claim 15 wherein each of said mechanical transducer elements comprises:
a load cell coupled to said support means and mechanically connected to said probe handle.

17. The prostate examination device of claim 16 wherein each of said mechanical transducer element comprises a load cell coupled to said support means and mechanically connected to said probe handle and said electronic unit further comprises:
a force sensing circuit responsive to the signals generated by said load cell for measuring the force imposed on each of said load cells of said positioning system.

18. The prostate examination device of claim 14 wherein said positioning system comprises:
a plurality of optical devices for generating signals in response to movements of said handle relative to said support means.

19. The prostate examination device of claim 18 wherein said each of optical devices comprises:
an opto-electronic pair having a receiving optical element coupled to said support means and a transmitting optical element connected to said handle.

20. The prostate examination device of claim 19 wherein said electronic unit comprises:
a distance sensing circuit responsive to the signals generated by said optical elements for determining the distance between said elements from the intensity of light received at said receiving elements and detecting the position of said probe relative to said support.

21. The prostate examination device of claim 14, wherein said positioning system comprises:
a plurality of capacitance transducers for generating signals in response to movements of said handle relative to said support means.

22. The prostate examination device of claim 21 wherein each of said capacitance transducers comprises:
a first electrode connected to said support means and a second electrode connected to said shaft for determining the distance between said first electrode and said second electrode.

23. The prostate examination device of claim 22 wherein said electronic unit further comprises:
a distance sensing circuit responsive to the signals generated by said capacitance transducers for detecting the position of said probe relative to said support.

24. The prostate examination device of claim 14 wherein said support means comprises:
a slot with a revolving locker for locking said probe in a working position.

25. The prostate examination device of claim 14 wherein said support means is connected to said probe with a ball and socket joint, said ball and socket joint providing rotational motion of said shaft.

26. The prostate examination device of claim 14 wherein said pressure sensor assembly comprises:
a plurality of flexing diaphragms containing strain gages bonded to an inner side of said flexing diaphragms.

27. The prostate examination device of claim 14 wherein said pressure sensor assembly comprises:
a plurality of flexing diaphragms positioned in a cylinder filled with an elastic compound, whereby strain gages are bonded to an inner side of said flexing diaphragms.

28. The prostate examination device of claim 14 wherein said pressure sensor assembly comprises:
a plurality of microfabricated pressure sensors integrated into a monolithic sensor-circuit chip and a sensing surface of said pressure sensors is covered with an elastic protective film.

29. The prostate examination device of claim 14 wherein said head comprises:
a biconvex sensing surface and a plurality of pressure sensors are arranged in a few lines along said biconvex sensing surface.

30. The prostate examination device of claim 14 wherein said head comprises:
a flat sensing surface and a plurality of pressure sensors arranged in a few lines along said flat sensing surface, and said sensing surface is inclined to an axis of said shaft.

31. A prostate examination device comprising:
a probe sized to fit within the rectum and having a head connected by a shaft to a handle;

a pressure sensor assembly coupled to said head for generating signals in response to forces imposed on said pressure sensor assembly as said pressure sensor assembly is pressed against and moved over the prostate;

a positioning system comprising a triaxial accelerometer; and an electronic unit for receiving said signals from said pressure sensor assembly and said position data from said positioning system and determining and displaying a structural image of said prostate from said pressure response signals and said position data.

32. The prostate examination device of claim 31 wherein said electronic unit comprises:
an acceleration sensing circuit responsive to the signals generated by said accelerometer for detecting accelerations;

a plurality of analog integrating circuits connected to said acceleration sensing circuit for detecting relative 3D motion of said probe during a prostate examination; and a storage device for storing results of the prostate examination.

* * * * *